United States Patent [19]
Wiersma

[11] Patent Number: 5,770,204
[45] Date of Patent: Jun. 23, 1998

[54] COMPOSITION FOR MUCOSA TREATMENT WITH SAPONIN

[75] Inventor: Jack G. Wiersma, Jupiter, Fla.

[73] Assignee: Nouveau Technologies, Inc., Tequesta, Fla.

[21] Appl. No.: 659,278

[22] Filed: Jun. 6, 1996

[51] Int. Cl.$^6$ ........................................... A61K 35/78
[52] U.S. Cl. ........................................ 424/195.1; 514/25
[58] Field of Search ........................... 424/195.1; 514/25

[56] References Cited

U.S. PATENT DOCUMENTS

| | | | |
|---|---|---|---|
| 4,657,766 | 4/1987 | Goodall | 426/309 |
| 5,139,779 | 8/1992 | McNeff | 424/195.1 |
| 5,468,492 | 11/1995 | Szaloki et al. | 424/195.1 |

*Primary Examiner*—Chhaya D. Sayala
*Attorney, Agent, or Firm*—McHale & Slavin, P.A.

[57] ABSTRACT

The instant invention is a composition based upon a triterpene saponin having a particular application for inclusion in the diets of vertebrates to reduce or eliminate the colonization of bacteria in the digestive and intestinal tracts of vertebrates, thereby creating a healthier mucosa and an overall healthier vertebrate.

7 Claims, No Drawings

COMPOSITION FOR MUCOSA TREATMENT WITH SAPONIN

FIELD OF THE INVENTION

This invention relates to a diet supplement and more particularly to use of a saponin for reducing or eliminating the colonization of bacteria in the digestive and intestinal tracts of vertebrates thereby creating a healthier mucosa.

BACKGROUND OF THE INVENTION

The subject matter of this patent is related to U.S. Patent Application entitled DECONTAMINATION PROCESS having Ser. No. 08/602232 filed Feb. 15, 1996, the contents of which are incorporated herein by reference as if fully restated.

Bacteria are a group of microscopic, unicellular organisms that lack a distinct nucleus and reproduce by cell division. Bacteria typically range from 1 to 10 micrometers and vary in the ways they obtain energy and nourishment. About 200 species of bacteria are pathogenic. Pathogenicity varies among the species and is dependent on both the virulence of the species and the condition of the host organism. The $E.\ coli$ 0157:H7 and salmonella microorganisms are just two of the most well known pathogenic bacteria which may cause death in vertebrates. Bacteria growth can also lead to food poisoning such as that caused by clostridiumbotulinum or staphylococcus aureus bacteria can be aerobes or anaerobes and are capable of attaching to any surface.

Under certain conditions bacteria can quickly form a microorganism which seeks a surface having nutrients for growth. As the microorganisms grow and multiply, the newly formed cells attach to each other as well as to the surface forming a confluent colony. When a colony becomes sufficiently large, it entraps nutrients and other microorganisms, wherein a microbial biofilm is established. A biofilm coating enhances the ability of bacteria to resist removal and inactivation. If a biofilm conceals a pathogenic bacteria, the result can lead to illness and death.

According to industry publications by Characklis and Cooksel in 1983 further supplemented by Characklis in 1984—set forth in Food Technology, Article of July 1994, Volume 48, No. 7 the biofilm is considered a five stage process which results from the physical, chemical and biological phenomenon and is identified as follows: transport of nutrients, inorganic and organic matter to the solid surface absorption of a conditioning film containing inorganic and organic nutrients attachment of microbial cells to the wetted surface in initiation of growth bacterial metabolism within the biofilm and cell disruption and detachment from the biofilm.

For these reasons, among others, including the ability of the vertebrates digestive and intestinal tracts to function efficiently, there has been a desire by both the food and pharmaceutical industries to address the colonization of bacteria in the digestive and intestinal tracts, the removal of unwanted pathogens, and improving the health of the mucosa, thereby creating a healthier condition for vertebrates.

In order to address these above mentioned concerns one must first determine a safe and efficacious method of the inclusion of a substance having multiple and desirable characteristics, ie: effective against both gram positive and gram negative pathogens, non-ionic surfactant characteristics, liquid surface reducing characteristics, a wide compatibility range, considered safe for inclusion by all vertebrates. Also, not causing any morphological changes in tissues or histological changes under histopathologic examination.

It further has been determined that the ability of bacteria to colonize in the digestive and intestinal tracts of vertebrates causes poor food and nutrient utilization, can cause gastrointestinal problems, diarrhea, and even death. Additionally it reduces dietary energy and intestinal absorption.

Thus, what is lacking in the art is the need for a composition capable of reducing or eliminating the colonization of bacteria in the intestinal tracts to create a healthier mucosa.

SUMMARY OF THE INVENTION

The instant invention is a composition based upon a saponin having a particular application for inclusion in the diets of vertebrates to reduce or eliminate the colonization of bacteria in the digestive and intestinal tracts of vertebrates, thereby creating a healthier mucosa and an overall healthier vertebrate.

The composition is a colloidal saponin that through biopsy studies proves does not harm the digestive or intestinal tract of a vertabrate. As further described later in this specification, studies conducted demonstrate there is no adverse effects from the inclusion of a triterpene saponin in the diets of poultry or swine. The studies demonstrated benefits relating to the overall improvement in the temperament and health when included in the diet. In these studies the triterpene saponin was incorporated in the diets at the inclusion rate of 4 to 5 oz per ton of feed, or added to the drinking water at a ratio between 10000:1 to 16000:1. The ratio amount will be dependant upon any masking effect of the carrier but should not need to exceed 20 ounces per ton when added to feed or more than a 20000:1 ratio when added to water. Owing to the surface reducing characteristics of saponin when villi is exposed to the saponin reduces surface tension to enable greater digestion and absorption of nutrients.

Thus, an objective of the invention is to improve the digestive and intestinal tract by forming a coating within the environment for reducing or eliminating the ability of bacteria to colonize. The composition based on a triterpene saponin that when added to the diet lowers the fluid surface tension resulting in a healthier intestinal mucosa for more complete and efficient digestion of food thereby making the host more resistant to low grade infections.

Another objective of the invention is to teach the use of a diet supplement having no morphological changes or significant alterations in tissues.

Still another objective of the invention is to teach the use of a diet supplement that is not harmful to the intestinal tract, demonstrates no histological changes, and enhances the mucosa of the digestive and intestinal tract.

Yet another objective of the invention is to teach the use of a diet supplement to provide a reduction in the occurrence of ascites to reduce or eliminate the administration of bacitracin and certain antibiotics.

Other objectives and advantages of this invention will become apparent from the following description and by way of example setting forth certain embodiments of this invention.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

For purposes of this invention, a triterpene saponin has been used as the preferred embodiment although, other saponins having similar characteristics have application. It is known that all saponins have similar characteristics however, they fall into generally three categories: triterpene, steroid, and steroid-alkaloid. Among the saponins isolated so far, the triterpenes represent a significant group and are commercially available. These are combinations with mostly 30-C atoms, which may be called mainly oleanan derivatives. By way of example, although not limited to, the triterpene saponins determined so far include up to 11 mono-saccharide units and are allodial. It has been further determined that all saponins are glucosides. In the U.S. the use of quillaya extract (a triterpene saponin) is permissible in food and beverages. It is registered by the F.D.A under 172.510 (GRAS LIST). In the United Kingdom the use of quillaya extract in food and beverages is permissible according to the Statutory Instruments 1975 No. 1486.

With this in mind, it has been determined by university tests and field trials that a saponin, for purposes of this invention, the preferred embodiment being a triterpene saponin, when included in the diet of vertebrates at various inclusion rates on a daily basis creates a coating in the digestive and intestinal tracts of vertebrates. As an example: it has been found that when a saponin was included at the rate of 3.8 oz. per ton of feed for poultry that the following conclusions, after histopathologic examination were determined under the direction of a recognized U.S. University's Diagnostic Laboratory:

1) After the inclusion of a triterpene saponin in the diets of poultry there were no morphological changes in tissues.

2) After the inclusion of a triterpene saponin in the diets of poultry there were no significant alterations in any of the tissues.

3) Multiple sections of duodenum, jejunum, cecum, colon, pancreas,, lung and trachea showed no morphological changes.

4) Based on the study, it was determined that the triterpene saponin was safe and efficacious.

5) The study further commented that in conclusion the triterpene saponin was not harmful to the intestinal tract, showed no histological changes, and may have even enhanced the health and well being of the intestinal tract.

Because the saponin is colloidal one can, with a high level of certainty, determine from the aforementioned biopsy study, that a triterpene saponin will not harm the vertebrates digestive and intestinal tracts. Accordingly, similar studies conducted at a recognized European University further demonstrated there were no adverse effects from the inclusion of a triterpene saponin in the diets of swine. In fact the numerous studies demonstrated definitive benefits relating to the overall improvement in the temperament and health of the swine when a triterpene saponin was included in the swine's diet. In these studies the triterpene saponin was incorporated in the diets at the inclusion rate of 4 to 5 oz per ton but less than 20 ounces per ton of feed. Understanding the colloidal, surfactant, emulsifying, and surface reduction characteristics of a saponin, then the following effects are realized when a saponin is included in the diets of vertebrates at various inclusion rates. "The digestive system is commonly referred to as the Alimentary Canal together with the associated digestive glands" (Harper Collins Biology Dictionary 1991). In vertebrates the digestive process begins within the mouth cavity where starch digestion occurs and then proceeds to the stomach where the start of protein digestion in acid conditions takes place. From the stomach food then proceeds to the small intestine which is the main area of digestion for all types of food.

The digestive process generally is referred to as digestion and is a process requiring enzymes in which complex food molecules are broken down by hydrolysis into a state which they can be absorbed. Digestion includes the physical events of chewing and emulsification besides chemical breakage of covalent bonds by mineral acids and enzymes. Food molecules are often too large to simply diffuse across cell membranes, and their digestion is required first. It further has been determined, in the literatures that in the small intestine there are microscopic projections called villi, which increase the surface area for digestion and absorption.

Owing to the surface reducing characteristics of saponin F-that when the villi is exposed to the saponin the reduction of surface tension enables for greater digestion and absorption of nutrients.

It is known that when food is ingested by vertebrates that bacteria, and many times unwanted pathogens, along with the food enters the digestive process. Owing to it's characteristics saponins create a more favorable atmosphere by producing a healthier digestive and intestinal tract condition. This has been demonstrated by university and supervised protocols under field conditions whereby the following determinations were made:

1) Broilers

| Area | % Improve Over Controls | | |
|---|---|---|---|
| | Gain | Feed/Gain | Mortality |
| Panama | 2.32 | 3.11 | 2.33 |
| South U.S. | 1.65 | 1.66 | 0.30 |
| East U.S. | 3.52 | 2.94 | 0.30 |
| South U.S. | −1.81 | 1.81 | 1.43 |
| South U.S. | 4.77 | 1.83 | −2.40 |
| Average | 2.09 | 2.27 | 0.43 |

2) Pullets

| Area | % Improvement Over Controls | |
|---|---|---|
| | Feed | Mortality |
| Mid-West | 8.63 | 0.34 |
| South U.S. | 2.89 | 3.99 |
| South U.S. | 10.45 | 6.03 |
| Southeast U.S. | 10.02 | 4.71 |
| Average | 7.99 | 3.76 |

3) Swine

| Area - Europe | Control | Test |
|---|---|---|
| Wt. Gain Per Day | 504 gr. | 620 gr. |
| Amount of Feed/kg | 17,400 kg | 16,920 kg |
| Feed for 1 kg of wt. | 4.0 kg | 3.6 kg |
| Gross wt. of Swine | 5,500 kg | 5,800 kg |

This test was performed on a total of 100 hogs, 50 in the control group and 50 in the test group. All swine lived to the end of the test. This test was summed up with the following comments: a) Compared with the control group the calmness of the treated animals was definitely more noticeable, b) With the treated group a more intensive food absorption was noted.

Additionally, there was the same consistency in differentiation between the control groups and test groups throughout the swine trials in Europe. It has been further noted that in numerous cases that there has been noticeable reduction in the occurrence of ascites in poultry along with the case of a major grower who has eliminated the administration of bacitracin altogether. European studies further noted a reduction in the need of certain antibiotics with respect to swine when a triterpene saponin was included in the daily diet.

Realizing the above it is clear that the inclusion of a triterpene saponin in the daily diet of vertebrates, at various inclusion rates, has demonstrated the results of creating an improved environment in which the digestive process occurs. The specific activity which takes place causing the aforementioned results is one which can be summed up in the following manner: Because of the triterpene saponin's non-ionic surfactant characteristics, it has been evidenced that when ingested, even at low daily inclusion rates, in conjunction with other foods, that it forms a coating in the digestive and intestinal tracts reducing or eliminating the ability of bacteria to colonize. In doing so the triterpene saponin has created a better environment for digestion by reducing or eliminating the bacteria, which when colonized, can disrupt the normal digestive process and can create gastrointestinal problems causing more digestive energy to be consumed, and a reduced ability to efficiently utilize the nutrients presented.

In conclusion, the mode of action of the triterpene saponin for enhanced vertebrate performance has not been completely delineated as of yet. However, it is theorized that the explanation is in response to the triterpene saponin's activity in the digestive tract—lowering fluid surface tension, resulting in a healthier mucosa. The end result then would be a more complete and efficient digestion of food, thus reflected in better gain and feed efficiency. Health improvement likely results from a generally healthier intestinal mucosa thereby making the host more resistant to low grade infections.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A mucosa treatment mixture for treating mucosa throughout a digestive tract comprising: a composition of 1 part colloidal non-steroidal saponin admixed to 20,000 parts water; whereby said composition is taken orally for purposes of reducing the ability of bacteria to colonize by reducing the fluid surface tension.

2. The composition according to claim 1 wherein said saponin is a triterpene.

3. The mucosa treatment mixture according to claim 1 for conditioning the mucosa of the digestive tract of a vertebrate in need of such conditioning by administering to a host a therapeutically effective amount of said composition.

4. The mucosa treatment mixture according to claim 1 for conditioning the mucosa of the intestinal tract of a vertebrate in need of such conditioning by administering to a host a therapeutically effective amount of said composition.

5. A mucosa treatment mixture for treating mucosa throughout a digestive tract comprising: a composition of from 4 up to 20 ounces of colloidal non-steroidal saponin admixed to 1 ton of livestock feed; whereby said composition is taken orally for purposes of coating and conditioning a digestive tract for reducing the ability of bacteria to colonize by reducing the fluid surface tension within the mucosa.

6. The mucosa treatment mixture according to claim 5 for conditioning the mucosa of the digestive tract of a vertebrate in need of such conditioning by administering to a host a therapeutically effective amount of said composition.

7. The mucosa treatment mixture according to claim 5 for conditioning the mucosa of the intestinal tract of a vertebrate in need of such conditioning by administering to a host a therapeutically effective amount of said composition.

* * * * *